(12) United States Patent
Guerin

(10) Patent No.: US 11,944,695 B2
(45) Date of Patent: Apr. 2, 2024

(54) COATED COLOURING SOLID PARTICLES COMPRISING AT LEAST ONE DIRECT DYE AND/OR ONE OXIDATION DYE PRECURSOR

(71) Applicant: L'OREAL, Paris (FR)

(72) Inventor: Frédéric Guerin, Saint Ouen (FR)

(73) Assignee: L'Oreal, Paris (FR)

(*) Notice: Subject to any disclaimer, the term of this patent is extended or adjusted under 35 U.S.C. 154(b) by 0 days.

(21) Appl. No.: 17/772,487

(22) PCT Filed: Oct. 27, 2020

(86) PCT No.: PCT/EP2020/080194
§ 371 (c)(1),
(2) Date: Apr. 27, 2022

(87) PCT Pub. No.: WO2021/083903
PCT Pub. Date: May 6, 2021

(65) Prior Publication Data
US 2023/0047506 A1 Feb. 16, 2023

(30) Foreign Application Priority Data
Oct. 28, 2019 (FR) ........................................ 1912067

(51) Int. Cl.
*A61Q 5/10* (2006.01)
*A61K 8/02* (2006.01)
(Continued)

(52) U.S. Cl.
CPC ............ *A61K 8/0245* (2013.01); *A61K 8/415* (2013.01); *A61K 8/44* (2013.01); *A61K 8/463* (2013.01);
(Continued)

(58) Field of Classification Search
CPC ........ A61K 8/0245; A61K 8/415; A61K 8/44; A61K 8/463; A61K 8/731; A61K 8/8152;
(Continued)

(56) References Cited

U.S. PATENT DOCUMENTS 5,017,195 A * 5/1991 Satou .................. C09B 67/0094
8/561
2006/0162097 A1 7/2006 Schmenger et al.
(Continued)

FOREIGN PATENT DOCUMENTS

WO       WO 0145653 A1 *  6/2001    ............... A61Q 5/10
WO       WO 2012/127429     9/2012

OTHER PUBLICATIONS

International Search Report dated Dec. 22, 2020, issued in corresponding International Patent Application No. PCT/EP2020/080194, filed Oct. 27, 2020, 3 pages.
(Continued)

*Primary Examiner* — Eisa B Elhilo
(74) *Attorney, Agent, or Firm* — Christensen O'Connor Johnson Kindness PLLC

(57) ABSTRACT

The present application relates to a colouring solid particle for dyeing keratin fibres, in particular human keratin fibres such as the hair, comprising a core containing one or more direct dyes and/or one or more oxidation dye precursors and an upper coating layer covering said core and containing one or more cellulose ethers. The present application also relates to a process for preparing a dye composition comprising one or more colouring solid particles, to a process for the oxidation dyeing of keratin fibres, comprising the application of the composition obtained to said fibres, and to the use of this composition for dyeing keratin fibres.

22 Claims, 1 Drawing Sheet

(51) Int. Cl.
*A61K 8/41* (2006.01)
*A61K 8/44* (2006.01)
*A61K 8/46* (2006.01)
*A61K 8/73* (2006.01)
*A61K 8/81* (2006.01)

(52) U.S. Cl.
CPC ............ *A61K 8/731* (2013.01); *A61K 8/8152* (2013.01); *A61K 8/8176* (2013.01); *A61Q 5/10* (2013.01); *A61K 2800/432* (2013.01)

(58) Field of Classification Search
CPC ............ A61K 8/8176; A61K 2800/432; A61K 8/0241; A61K 2800/4324; A61K 2800/624; A61K 2800/652; A61K 8/347; A61K 8/411; A61K 2800/31; A61Q 5/10
USPC ............................................................ 8/405
See application file for complete search history.

(56) References Cited

U.S. PATENT DOCUMENTS

| | | | |
|---|---|---|---|
| 2011/0247149 A1 | 10/2011 | Welz et al. | |
| 2015/0157539 A1* | 6/2015 | Shimizu | A61K 8/8152 424/59 |
| 2015/0190320 A1* | 7/2015 | Tachon | A61K 8/0279 424/59 |
| 2015/0290090 A1* | 10/2015 | Matsufuji | A61K 8/0279 424/59 |
| 2016/0030304 A1* | 2/2016 | Nagamatsu | A61Q 19/08 424/59 |

OTHER PUBLICATIONS

Written Opinion dated May 6, 2021, issued in corresponding International Patent Application No. PCT/EP2020/080194, filed Oct. 27, 2020, 7 pages.

* cited by examiner

COATED COLOURING SOLID PARTICLES COMPRISING AT LEAST ONE DIRECT DYE AND/OR ONE OXIDATION DYE PRECURSOR

The present application relates to a colouring solid particle for dyeing keratin fibres, in particular human keratin fibres such as the hair, comprising a core containing one or more direct dyes and/or one or more oxidation dye precursors and an upper coating layer covering said core and containing one or more cellulose ethers.

The present application also relates to a process for preparing a dye composition comprising one or more colouring solid particles, to a process for dyeing keratin fibres comprising the application of the composition obtained to said fibres and to the use of this composition for dyeing keratin fibres.

It is known practice to dye keratin fibres and in particular human hair with dye compositions containing oxidation dye precursors, such as oxidation bases, notably ortho- or para-phenylenediamines, ortho- or para-aminophenols and heterocyclic compounds. These oxidation bases are colourless or weakly coloured compounds, which, when combined with oxidizing products, are able to produce coloured compounds by a process of oxidative condensation.

It is also known that the shades obtained with these oxidation bases may be varied by combining them with couplers or colour modifiers, the latter being notably chosen from aromatic meta-diaminobenzenes, meta-aminophenols, meta-diphenols and certain heterocyclic compounds such as indole compounds.

The variety of molecules used as oxidation bases and couplers allows a wide range of colours to be obtained.

At the present time, it is difficult to customize the permanent dyeing of keratin fibres. Specifically, a user wishing to dye his or her hair only has a choice from a catalogue of predefined dye compositions, each generally comprising a set mixture of oxidation base(s) and of oxidation couplers(s) in predefined contents.

Thus, each of these dye compositions makes it possible to obtain only one colour shade and the user has a choice from only a limited number of shades preselected by the manufacturers, which do not always correspond to his or her desires.

Furthermore, the predefined dye compositions do not always lead exactly to the production of the corresponding preselected shade: as a function of the natural shade (more or less light or dark) and of the condition of the user's hair (more or less damaged or sensitized), the final rendering in terms of colouring may vary substantially from one user to another.

The current oxidation dye compositions thus do not make it possible rapidly to obtain (for example during a user's appointment at the hair salon) customized colourings as a function of the pre-existing shade of the user's keratin fibres, or according to his or her desires.

There is thus a real need to develop novel solutions for preparing, just before dyeing, compositions for dyeing keratin fibres which makes it possible to offer the user a very wide choice of possible shades, and enabling him or her to be able to choose, for example in a hair salon, the shade that he or she desires rather than as a default the closest available shade.

There is also a need for solutions for preparing, just before dyeing, customized dye compositions, notably taking into account the specificities of each user such as the pre-existing shade and the nature of the keratin fibres.

Moreover, processes are still sought which are capable of dyeing keratin fibres in an intense, fast, sparingly selective and chromatic manner, with good build-up of the colour, and which are capable of giving colourings that are resistant to the various attacking factors to which the fibres may be subjected, such as bad weather, washing and perspiration.

These aims are achieved with the present invention, one subject of which is notably a colouring solid particle, having a volume of between 25 mm$^3$ and 125 mm$^3$, and comprising:
  a. a core containing one or more dyes chosen from direct dyes and/or oxidation dye precursors; and
  b. an upper coating layer covering said core, and containing one or more cellulose ethers.

It has been found that the colouring solid particles according to the invention enable personalized colourings of keratin fibres to be obtained.

Specifically, the colouring solid particles make it possible to prepare, for each use, a specific dye composition containing precise amounts of dyes specifically chosen so as to obtain the exact shade desired by the user.

It has notably been found that the colouring solid particles make it possible to prepare compositions that are capable of combining a very large number of different dyes, in different respective contents, and thus to dye the keratin fibres in a very wide range of possible colours while at the same time taking into account the nature and the specific condition of the fibres of each user.

The colouring solid particles according to the invention also make it possible to satisfactorily dye keratin fibres, notably producing powerful, fast, chromatic and sparingly selective colourings, and/or colourings with good colour build-up.

Moreover, the colouring solid particles according to the invention lead to colourings that are resistant to the various attacking factors to which keratin fibres may be subjected, such as bad weather, light, washing and/or perspiration.

Moreover, the colouring solid particles according to the invention give a reproducible dyeing result time after time, the solid particles containing one or more direct dyes and/or one or more oxidation dye precursors having very good stability on storage. Furthermore, the solid particles according to the invention disintegrate rapidly and lead quickly and easily to a homogeneous mixture when they are mixed with at least one aqueous composition.

Furthermore, it has been found that the particles according to the invention obtained by a direct compression process exhibit good dissolution in an aqueous composition.

A subject of the invention is also a process for preparing an aqueous dye composition, comprising the mixing of one or more colouring solid particles according to the invention with at least one aqueous composition.

A subject of the invention is also a process for dyeing keratin fibres, in particular human keratin fibres such as the hair, comprising:
  the preparation of an aqueous dye composition according to the preparation process of the invention; and then
  the application of said prepared composition to said keratin fibres.

A subject of the invention is also the use of the aqueous dye composition obtained via the preparation process according to the invention, for dyeing keratin fibres, in particular human keratin fibres such as the hair.

Other subjects, characteristics, aspects and advantages of the invention will emerge even more clearly on reading the description and the example that follows.

In the present description, and unless otherwise indicated:
the expression "at least one" is equivalent to the expression "one or more" and can be replaced therewith;
the expression "between" is equivalent to the expression "ranging from" and can be replaced therewith, and implies that the limits are included;
the term "keratin fibres", according to the present application, preferably denotes human keratin fibres and more particularly the hair.

The Solid Particles

The colouring solid particle according to the invention comprises a core containing one or more dyes chosen from direct dyes and/or oxidation dye precursors, and an upper coating layer covering said core, preferably totally, and containing one or more cellulose ethers.

In the core, said direct dyes and/or oxidation dye precursors may be identical or different in the core of the same particle and from one solid particle to another.

According to a particular embodiment, the particle comprises only one or several direct dyes. According to another embodiment, the particle comprises only one or several oxidation dye precursors, preferably only one oxidation dye precursor. According to a third embodiment, the particle contains one or more direct dyes and one or more oxidation dye precursors, preferably only one oxidation dye precursor.

According to a particular embodiment, the particles are identical or different but correspond to the various embodiments described above.

Advantageously, the dye(s) are chosen from oxidation dye precursors; preferably from oxidation bases and oxidation couplers; even more preferentially from oxidation bases.

For the purposes of the invention, the term "solid particle" means a particle which is in solid form at room temperature (25° C.) and at atmospheric pressure ($1.013 \times 10^5$ Pa).

Advantageously, the direct dye(s) and/or the oxidation dye precursor(s) represent from 0.001% to 50% by weight, preferably from 0.1% to 50% by weight, more preferentially from 0.3% to 25% by weight and even more preferentially from 0.4% to 22% by weight, relative to the total weight of the solid particle containing same.

Preferably, the colouring solid particle according to the invention comprises, in the core, only one oxidation dye precursor; and more preferably in a content of between 0.1% and 50% by weight, even more preferentially from 0.3% to 25% by weight and better still from 0.4% to 22% by weight, relative to the total weight of the solid particle containing same.

BRIEF DESCRIPTION OF THE DRAWINGS

The attached drawings are schematic. The drawings are not necessarily to scale; they are above all intended to illustrate the principles of the invention. In these drawings, from FIG. 1 to FIG. 2, elements (or parts of an element) that are identical are identified by the same reference signs.

DETAILED DESCRIPTION OF THE DRAWINGS

Examples of implementation of the colouring solid particles are described in detail hereinbelow, with reference to the attached drawings. These examples illustrate the characteristics and the advantages of the invention. It is recalled, however, that the invention is not limited to these examples.

Figure 1:
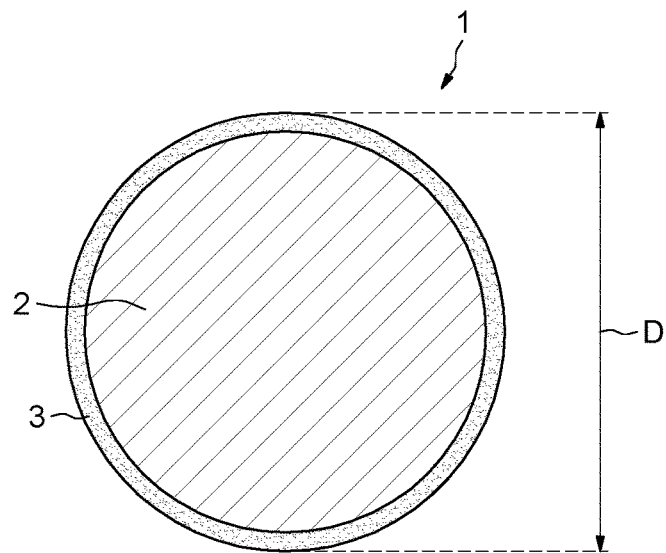
FIG. 1 represents a view in transverse cross section of a colouring solid particle in the form of a sphere according to one embodiment of the invention.

FIG. 1 represents a view in transverse cross section of a colouring solid particle 1 in the form of a sphere according to one embodiment of the invention, comprising a core 2 containing a dye, and an upper coating layer 3 containing cellulose ethers and totally covering said core 2.

For example, said dye may be an oxidation dye precursor.

The length D represented in FIG. 1 corresponds to the height of the colouring solid particle 1.

Figure 2:
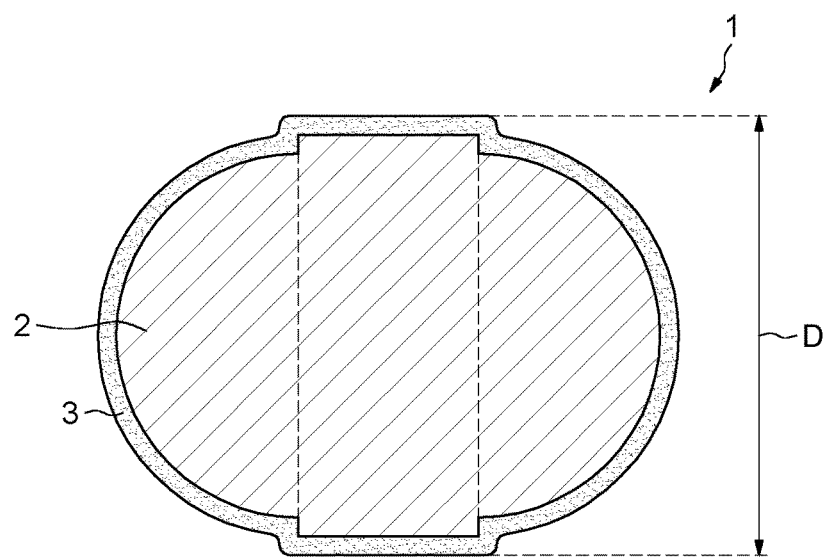
FIG. 2 represents a view in longitudinal cross section of another colouring solid particle in the form of a spheroid according to another embodiment of the invention.

FIG. 2 represents a view in longitudinal cross section of another colouring solid particle in the form of a spheroid according to another embodiment of the invention, comprising a core 2 containing a dye.

For example, said dye may be an oxidation dye precursor.

In FIG. 2, the particle 1 according to the invention also comprises an upper coating layer 3 totally covering said core 2 and containing cellulose ethers.

The length D represented in FIG. 2 corresponds to the height of the colouring solid particle 1.

The Oxidation Dye Precursors

Preferably, the oxidation dye precursor(s) are chosen from oxidation bases and oxidation couplers; more preferentially from oxidation bases.

Preferably, the total content of oxidation dye precursor(s) present in said core of the colouring solid particle according to the invention represents from 0.1% to 50% by weight, more preferentially from 0.3% to 25% by weight, even more preferentially from 0.4% to 22% by weight, relative to the total weight of the solid particle containing same.

By way of example, the oxidation bases are chosen from para-phenylenediamines, bis(phenyl)alkylenediamines, para-aminophenols ortho-aminophenols and heterocyclic bases, and the corresponding addition salts.

Among the para-phenylenediamines that may be mentioned are, for example, para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-methoxymethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the corresponding addition salts with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the corresponding addition salts with an acid, are particularly preferred.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the corresponding addition salts.

Among the para-aminophenols that are mentioned are, for example, para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the corresponding addition salts with an acid.

Among the ortho-aminophenols that may be mentioned, for example, are 2-aminophenol, 2-amino-5-methylphenol, 2-amino-6-methylphenol and 5-acetamido-2-aminophenol, and the corresponding addition salts.

Among the heterocyclic bases that may be mentioned, for example, are pyridine, pyrimidine and pyrazole derivatives.

Among the pyridine derivatives that may be mentioned are the compounds described, for example, in patents GB 1 026 978 and GB 1 153 196, for example 2,5-diaminopyridine, 2-(4-methoxyphenyl)amino-3-aminopyridine and 3,4-diaminopyridine, and the corresponding addition salts.

Other pyridine oxidation bases that are useful in the present invention are the 3-aminopyrazolo[1,5-a]pyridine oxidation bases or the corresponding addition salts described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-β-hydroxyethoxy-3-aminopyrazolo[1,5-a]pyridine and 2-(4-dimethylpiperazinium-1-yl)-3-aminopyrazolo[1,5-a]pyridine, and the corresponding addition salts.

More particularly, the oxidation bases that are useful in the present invention are chosen from 3-aminopyrazolo[1,5-a]pyridines and are preferably substituted on carbon atom 2 with:

a) a (di)($C_1$-$C_6$)(alkyl)amino group, said alkyl group possibly being substituted with at least one hydroxyl, amino or imidazolium group;

b) an optionally cationic 5- to 7-membered heterocycloalkyl group comprising from 1 to 3 heteroatoms, optionally substituted with one or more ($C_1$-$C_6$)alkyl groups such as a di($C_1$-$C_4$)alkylpiperazinium group; or c) a ($C_1$-$C_6$)alkoxy group optionally substituted with one or more hydroxyl groups, such as a β-hydroxyalkoxy group, and the corresponding addition salts.

Among the pyrimidine derivatives that may be mentioned are the compounds described, for example, in patents DE 2359399; JP 88-169571; JP 05-63124; EP 0770375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof and the tautomeric forms thereof, when a tautomeric equilibrium exists.

Among the pyrazole derivatives that may be mentioned are the compounds described in patents DE 3843892 and DE 4133957 and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the corresponding addition salts. Use may also be made of 4,5-diamino-1-(β-methoxyethyl)pyrazole.

A 4,5-diaminopyrazole will preferably be used and even more preferentially 4,5-diamino-1-(β-hydroxyethyl)pyrazole and/or a corresponding salt.

The pyrazole derivatives that may also be mentioned include diamino-N,N-dihydropyrazolopyrazolones and in particular those described in patent application FR-A-2 886 136, such as the following compounds and the corresponding addition salts: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-bis(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one and 2,3-diamino-6-hydroxy-6,7-dihydro-1H,5H-pyrazolo[1,2-a]pyrazol-1-one.

Use will preferably be made of 2,3-diamino-6,7-dihydro-1H,5H-pyrazolo[1,2-a]pyrazol-1-one and/or a corresponding salt.

Heterocyclic bases that will preferably be used are 4,5-diamino-1-(β-hydroxyethyl)pyrazole and/or 2,3-diamino-6, 7-dihydro-1H,5H-pyrazolo[1,2-a]pyrazol-1-one and/or 2-β-hydroxyethoxy-3-aminopyrazolo[1,5-a]pyridine and/or a corresponding salt.

According to a preferred embodiment of the invention, the core of the colouring solid particle according to the invention contains one or more oxidation bases; preferably only one oxidation base; more preferentially chosen from para-phenylenediamines, bis(phenyl)alkylenediamines, para-aminophenols ortho-aminophenols and heterocyclic bases, and the corresponding addition salts; even more preferentially from para-phenylenediamine, para-toluenediamine, para-aminophenol, N,N-bis(β-hydroxyethyl)-para-phenylenediamine, 4,5-diamino-1-(β-hydroxyethyl)pyrazole, 2,3-diamino-6,7-dihydro-1H,5H-pyrazolo[1,2-a]pyrazol-1-one, 2-β-hydroxyethoxy-3-aminopyrazolo[1,5-a]pyridine, and the addition salts thereof.

Preferably, when the oxidation dye precursor(s) present in the core of the colouring solid particle according to the invention are oxidation bases, the oxidation base(s) represent from 0.1% to 50% by weight, more preferentially from 0.3% to 25% by weight, even more preferentially from 0.4% to 22% by weight, relative to the total weight of the solid particle containing same.

By way of example, the oxidation couplers may be chosen from meta-phenylenediamines, meta-aminophenols, meta-diphenols, naphthalene-based coupling agents and heterocyclic coupling agents, and also the geometrical or optical isomers thereof, the tautomers thereof, the corresponding addition salts or the solvates thereof according to the invention.

Mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(p-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, 2-methyl-5-aminophenol, 5-N-(β-hydroxyethyl)amino-2-methylphenol, 3-aminophenol, 3-amino-2-chloro-6-methylphenol and 2-[3-amino-4-methoxyphenyl]amino)ethanol, and the corresponding addition salts with an acid.

According to a preferred embodiment of the invention, the core of the colouring solid particle according to the invention contains one or more oxidation couplers; preferably only one oxidation coupler; more preferentially chosen from meta-phenylenediamines, meta-aminophenols, meta-diphenols, naphthalene-based coupling agents, heterocyclic coupling agents, the corresponding addition salts thereof or the solvates thereof; even more preferentially from 1,3-dihydroxybenzene, 1,3-dihydroxy-2-methylbenzene, 3-aminophenol, 6-hydroxybenzomorpholine, 5-N-(β-hydroxyethyl)amino-2-methylphenol, 2,4-diamino-1-(β-hydroxyethyloxy)benzene, 2-methyl-5-aminophenol, 6-hydroxyindole, 4-chloro-1,3-dihydroxybenzene, 2-amino-3-hydroxypyridine, 3-amino-2-chloro-6-methylphenol, α-naphthol, 2-[3-amino-4-methoxyphenyl]amino)ethanol and the addition salts thereof.

Preferably, when the oxidation dye precursor(s) present in the core of the colouring solid particle according to the invention are oxidation couplers, the oxidation coupler(s) represent from 0.1% to 50% by weight, more preferentially from 0.3% to 25% by weight, even more preferentially from 0.4% to 22% by weight, relative to the total weight of the solid particle containing same.

In general, the addition salts of oxidation bases or of oxidation couplers that may be used in the context of the invention are chosen in particular from the addition salts with an acid such as the hydrochlorides, hydrobromides, sulfates, citrates, succinates, tartrates, lactates, tosylates, benzenesulfonates, phosphates and acetates.

The Direct Dyes

When the core of the solid particle according to the invention comprises one or more direct dyes, these direct dyes may be cationic, anionic, nonionic, and mixtures thereof; more preferentially, the direct dyes are chosen from cationic and nonionic direct dyes and mixtures thereof.

The direct dyes may be synthetic or natural.

Examples of suitable direct dyes that may be mentioned include azo direct dyes; (poly)methine dyes such as cyanines, hemicyanines and styryls; carbonyl dyes; azine dyes; nitro(hetero)aryl dyes; tri(hetero)arylmethane dyes; porphyrin dyes; phthalocyanine dyes and natural direct dyes, alone or in the form of mixtures.

Mention may notably be made, by way of example, of the dyes described in patent applications WO 95/15144, WO 95/01772 and EP-714954.

In particular, the useful direct dyes may be chosen from Basic Red 51, Basic Yellow 87 and Basic Orange 31 or corresponding derivatives:

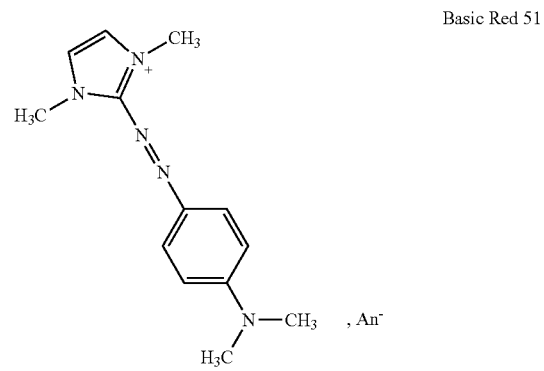

Basic Red 51

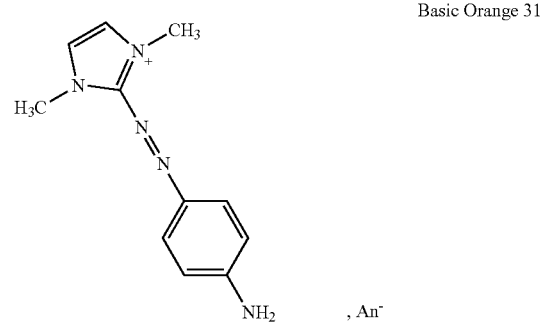

Basic Orange 31

-continued

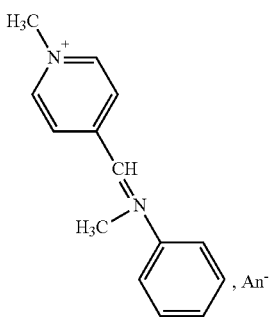

Basic Yellow 87

Among the natural direct dyes that may be used according to the invention, mention may be made of hennotannic acid, juglone, alizarin, purpurin, carminic acid, kermesic acid, purpurogallin, protocatechaldehyde, indigo, isatin, curcumin, spinulosin, apigenidin and orcein. Extracts or decoctions containing these natural dyes and in particular henna-based poultices or extracts may also be used.

Preferably, when the direct dye(s) are present in the core of the colouring solid particle according to the invention, the direct dye(s) advantageously represent 0.001% to 10% by weight, more preferentially 0.005% to 5% by weight, relative to the total weight of said solid particles.

The Binders

The core of the solid particle according to the invention also preferably comprises at least one binder.

For the purposes of the invention, the term "binder" means a compound which contributes towards the cohesion of the solid particle. The binder notably enables the agglomeration of the various components constituting the solid particle.

Examples of binders that may notably be mentioned include proteins (such as gelatin); saccharides and derivatives thereof, oligosaccharides and derivatives thereof including disaccharides (such as sucrose and lactose), notably in the anhydrous or hydrated forms thereof, and sugar alcohols (such as xylitol, sorbitol and maltitol); polyvinyl alcohol (PVA); polysaccharides and derivatives thereof (for example starches, cellulose and/or modified cellulose); alginate; and gums (for example acacia gum or guar gum).

Examples of suitable modified celluloses include microcrystalline cellulose (MCC), notably in the anhydrous or hydrated forms thereof, and cellulose ethers such as hydroxypropylcellulose (HPC) and hydroxypropylmethylcellulose (HPMC).

Preferably, the binder(s) are chosen from saccharides and derivatives thereof, oligosaccharides and derivatives thereof, polysaccharides and derivatives thereof, polyvinyl alcohol (PVA), and mixtures thereof; more preferentially from lactose, notably in anhydrous or hydrated form, microcrystalline cellulose (MCC), notably in anhydrous or hydrated form, polyvinyl alcohol (PVA), cellulose ethers such as hydroxypropylcellulose (HPC) and hydroxypropylmethylcellulose (HPMC), and mixtures thereof.

Preferably, when the binder(s) are present in the core of the solid particle according to the invention, the total content of binder(s) in said core is greater than or equal to 30% by weight; more preferentially greater than or equal to 50% by weight; even more preferentially between 50% and 99.9% by weight, better still between 60% and 99.9% by weight, even better still between 70% and 99.9% by weight, relative to the total weight of the solid particle containing same.

The Disintegrants

The core of the solid particle according to the invention also preferably comprises at least one disintegrant.

For the purposes of the present invention, the term "disintegrant" refers to a class of agents, preferably a class of polymers, which are particularly effective for inducing the disintegration of a solid particle (for example a tablet). One particular category of disintegrants is known as "superdisintegrants" since they are generally effective at low concentrations.

Disintegrants may be hygroscopic compounds which act by absorbing the liquid of a medium when they are placed in contact with said medium (for example the water of an aqueous medium). Such an absorption may then induce disintegration by bringing about considerable swelling of the disintegrant and/or by reinforcing the capillary action. The swelling pressure exerted by a disintegrant swollen in an external or radial direction can bring about the splitting of a solid particle (for example a tablet).

Examples of disintegrants, or even of superdisintegrants, that may notably be mentioned include crosslinked celluloses such as croscarmellose (or crosslinked carboxymethylcellulose, which is generally used in sodium salt form) and derivatives thereof, sold, for example, under the references Ac-Di-Sol®, Explocel®, Nymcel ZSX®, Pharmacel® XL, Primellose®, Solutab® and Vivasol®; crospovidone (or crosslinked polyvinylpyrrolidone) and derivatives thereof, sold, for example, under the references Crospovidone M®, Kollidon® and Polyplasdone®; crosslinked starch such as sodium starch glycolate, sold, for example, under the references Explotab®, Explotab® CLV, Explosol®, Primojel®, Tablo® and Vivastar®; crosslinked alginic acids, sold, for example, under the reference Satialgine®; crosslinked polyacrylic compounds such as ion-exchange resins, sold, for example, under the references Indion® 414, Tulsion® 339 and Amberlite® IRP; and certain polysaccharides, such as soybean polysaccharide, sold, for example, under the reference Emcosoy® superdisintegrant.

Preferably, the disintegrant(s) are polymeric; more preferentially, the solid particle comprises at least one disintegrant polymer, better still at least one superdisintegrant polymer; even more preferentially at least one superdisintegrant polymer chosen from crosslinked polymers of vinylpyrrolidone and derivatives thereof, and mixtures thereof; better still from crosslinked polyvinylpyrrolidones, crosslinked copolymers of vinylpyrrolidone/vinyl acetate, and mixtures thereof.

Preferably, when the disintegrant(s) are present in the core of the solid particle according to the invention, the total content of disintegrant(s) in said core is between 0.5% and 15% by weight, more preferentially between 1% and 12% by weight, and even more preferentially between 2% and 10% by weight, relative to the total weight of the solid particle containing same.

The Antioxidants

The core of the solid particle according to the invention also preferably comprises at least one antioxidant.

Examples of antioxidants that may notably be mentioned include ascorbic acid, salts thereof and derivatives thereof (such as sodium ascorbate, erythorbic acid, ascorbyl palmitate or ascorbyl laurate); salicylic acid, salts thereof and derivatives thereof (such as sodium salicylate); mercaptans and inorganic sulfites (such as sodium sulfite, sodium bisulfite, sodium metabisulfite, potassium sulfite and thioglycolic acid); 2,6-di-tert-butyl-4-methylphenol (BHT); butylated hydroxyanisole (BHA); sodium dithionite; and mixtures thereof.

Preferably, the antioxidants are chosen from ascorbic acid, salts thereof and derivatives thereof (such as sodium ascorbate, erythorbic acid, ascorbyl palmitate or ascorbyl laurate); salicylic acid, salts thereof and derivatives thereof (such as sodium salicylate); mercaptans and inorganic sulfites (such as sodium sulfite, sodium bisulfite, sodium metabisulfite, potassium sulfite and thioglycolic acid), and mixtures thereof; more preferentially from ascorbic acid, sodium sulfite, sodium bisulfite, sodium metabisulfite and sodium salicylate, and mixtures thereof.

Preferably, when the antioxidant(s) are present in the core of the solid particle according to the invention, the total content of antioxidant(s) in said core is between 0.1% and 15% by weight, more preferentially between 0.3% and 12% by weight, even more preferentially between 0.4% and 10% by weight, even better still between 0.5% and 5% by weight, relative to the total weight of the solid particle containing same.

Lubricants and/or Nonstick Agents

The core of the solid particle according to the invention also preferably comprises at least one lubricant and/or nonstick agent.

For the purposes of the invention, the term "lubricant and/or nonstick agent" means a compound for reducing, or even preventing, the agglomeration of the ingredients of the solid particles, for reducing the adhesion (notably during a compression step) and/or for improving the flow of the ingredients of the solid particles by reducing the friction and the cohesion between the ingredients.

Preferably, the lubricant(s) and/or nonstick agent(s) are chosen from magnesium stearate, calcium silicate, magnesium silicate, magnesium carbonate, silicon dioxide, talc, silica, stearic acid, sodium stearoyl fumarate, and mixtures thereof; more preferentially from silica, magnesium stearate, and mixtures thereof.

Preferably, when the lubricant(s) and/or nonstick agent(s) are present in the core of the solid particle according to the invention, the total content of lubricant(s) and/or nonstick agent(s) in said core is between 0.1% and 10% by weight, more preferentially between 0.3% and 8% by weight, and even more preferentially between 0.5% and 5% by weight, relative to the total weight of the solid particle containing same.

The Upper Coating Layer

The solid particles according to the invention comprise an upper coating layer (also known as an upper film layer) covering the core, preferably totally.

The upper coating layer according to the invention may optionally comprise one or more cellulose ethers such as those described previously.

The upper coating layer according to the invention may optionally comprise one or more other compounds such as polyethylene glycol (PEG); polyvinyl alcohol (PVA); polyvinylpyrrolidone (PVP); copolymers thereof (for example a copolymer of polyvinyl alcohol-polyethylene glycol PVA/PEG); sugars such as xanthan; and mixtures thereof.

Preferably, the upper coating layer comprises at least two different cellulose ethers.

According to a preferred embodiment of the invention, the upper coating layer comprises at least one cellulose ether as described previously; more preferentially a cellulose ether chosen from carboxymethylcellulose (CMC), ethylcellulose (EC), hydroxypropylcellulose (HPC), hydroxypropylmethylcellulose (HPMC), methylhydroxyethylcellulose (MHEC), and mixtures thereof, better still from hydroxypropylcellulose (HPC), hydroxypropylmethylcellulose (HPMC), and mixtures thereof.

More preferentially, the upper coating layer comprises hydroxypropylcellulose (HPC) and hydroxypropylmethylcellulose (HPMC).

Preferably, according to this embodiment of the invention, the total content of cellulose ether(s) present in the upper coating layer represents from 30% to 99% by weight; more preferentially from 40% to 90% by weight, even more preferentially from 45% to 80% by weight and better still from 50% to 70% by weight, relative to the total weight of the upper coating layer.

According to another preferred embodiment according to the invention, the upper coating layer comprises at least one lubricant and/or nonstick agent such as those described previously; more preferentially at least one lubricant and/or nonstick agent chosen from calcium silicate, magnesium silicate, magnesium carbonate, silicon dioxide, talc, silica, and mixtures thereof; more preferentially, the lubricant and/or nonstick agent is talc.

Preferably, according to this embodiment, the total content of lubricant(s) and/or nonstick agent(s) present in the upper coating layer is between 1% and 40% by weight, more preferentially between 2% and 30% by weight, relative to the total weight of the upper coating layer.

Preferably, the upper coating layer according to the invention also comprises one or more pigments.

By way of example, the pigments may be white or coloured, mineral and/or organic, and coated or uncoated. Among the mineral pigments that may be mentioned are metal oxides, in particular titanium dioxide, optionally surface-treated, zirconium oxide, zinc oxide or cerium oxide, and also iron oxide, titanium oxide or chromium oxide, manganese violet, ultramarine blue, ultramarine pink, chromium hydrate and ferric blue, and mixtures thereof. Among the organic pigments that may be mentioned are carbon black, pigments of D & C type and lakes based on cochineal carmine or on barium, strontium, calcium or aluminium, and mixtures thereof.

According to a preferred embodiment of the invention, the upper coating layer according to the invention also comprises one or more pigments chosen from zirconium oxides, zinc oxides, cerium oxides, iron oxides, titanium oxides, chromium oxides, manganese violet, ultramarine blue, ultramarine pink, chromium hydrate and ferric blue, and mixtures thereof; more preferentially one or more pigments chosen from titanium oxides such as titanium dioxide, iron oxides, chromium oxides, notably green chromium oxide, and mixtures thereof.

When the upper coating layer comprises one or more pigments, the pigment(s) advantageously represent a total content ranging from 1% to 50% by weight, more preferentially 5% to 40% by weight, relative to the total weight of the upper coating layer.

Preferably, the colouring solid particles according to the invention are anhydrous.

The term "anhydrous colouring solid particle" means that the solid particle contains less than 2% by weight of water, preferably less than 1% by weight of water, and even more preferentially less than 0.5% by weight of water relative to the total weight of the solid particle, or even said solid particle is free of water. In particular, the water that may be present is not added during the preparation of the solid particle, but corresponds to the residual water provided by the mixed ingredients.

The solid particles according to the invention may advantageously be in a spherical or spheroidal form; more preferentially in a spherical form, such as in the form of a bead.

The colouring solid particle according to the invention has a volume of between 25 mm³ and 125 mm³, preferably between 30 and 90 mm³, even more preferentially between 45 and 65 mm³.

For the purposes of the invention, the volume V of the solid particle according to the invention may notably be calculated by means of the following equation:

$$V=(1/6)\cdot\pi\cdot D^3$$

in which D represents the height of the solid particle according to the invention.

The height D of a particle according to the invention is notably illustrated in FIGS. 1 and 2. It may be measured in particular using a ruler, a vernier caliper, or any other measuring instrument conventionally used for measuring a length.

Preferably, the height D of a solid particle according to the invention is measured using a vernier caliper.

In addition, the mean volume $V_m$ of a population of solid particles according to the invention, in particular of at least 10 particles, may notably be calculated by means of the following equation:

$$V_m=(1/6)\cdot\pi\cdot D_m^3$$

in which $D_m$ represents the mean height of the solid particles according to the invention.

The mean height $D_m$ of the solid particles according to the invention may be calculated by determining the mean of at least 10 heights D measured on at least 10 different colouring solid particles.

Preferably, the mean volume of said colouring solid particles according to the invention is between 25 and 125 mm³, more preferentially between 30 and 90 mm³, even more preferentially between 45 and 65 mm³.

Preferably, the colouring solid particle according to the invention has a mass of between 30 and 120 mg, more preferentially between 40 and 80 mg, even more preferentially between 50 and 70 mg.

In addition, the mean mass of the colouring solid particles according to the invention is preferably between 30 and 120 mg, more preferentially between 40 and 80 mg, even more preferentially between 50 and 70 mg.

The mean mass of the solid particles according to the invention may be calculated by determining the mean of at least 10 weighings of at least 10 different colouring solid particles.

Preferably, the hardness of the colouring solid particle according to the invention is between 2 and 15 kPa, more preferentially between 2 and 11 kPa.

The hardness of a solid particle may be measured, for example, using a semiautomatic tablet testing system commonly used in the pharmaceutical field, notably using the Pharmatron ST50 device.

In addition, the mean hardness of the colouring solid particles according to the invention is preferably between 2 and 15 kPa, more preferentially between 2 and 11 kPa.

The mean hardness of the solid particles according to the invention may be calculated by determining the mean of at least 10 hardnesses measured on at least 10 different colouring solid particles.

Preferably, the solid particles have a mean disintegration time in 25 mL of aqueous hydrogen peroxide solution (containing 6% by weight of $H_2O_2$) at 25° C. and at atmospheric pressure of less than 60 seconds, more preferentially less than 40 seconds, better still between 1 and 30 seconds.

By way of example, the mean disintegration time may be measured according to the following method:
1) 25 mL of an aqueous oxidizing composition comprising 6% by weight of hydrogen peroxide are poured into a 50 mL beaker; and then
2) 10 identical colouring solid particles according to the invention are added in a single portion; the contents of the beaker are not stirred; and then
3) the chronometer is started;
4) the chronometer is stopped, once all the solid particles are visually fully deaggregated, i.e. once it is observed that the solid particles form a soft mass no longer containing a firm core; and finally
5) the mean disintegration time on the chronometer is recorded.

Preferably, the upper coating layer according to the invention represents a content of from 0.1% to 10% by weight, more preferentially from 0.5% to 10% by weight and better still from 1% to 5% by weight relative to the total weight of the solid particle.

Preferably, the weight ratio of the total mass of the colouring solid particle according to the invention, on the one hand, to the total mass of the core of said solid particle, on the other hand, is between 1.001 and 1.1, more preferentially between 1.005 and 1.1; even more preferentially between 1.01 and 1.05.

The solid particles according to the invention are advantageously prepared according to the conventional processes for preparing tablets, which may be film-coated, such as the processes used in the pharmaceutical industry, notably via a dry route or by wet granulation.

More particularly, the solid particles according to the invention may be prepared via a dry route according to the following steps:
milling of the direct dyes and/or of the oxidation dye precursors, and of the other optional ingredients of the solid particle; and then
screening of the powder obtained; and then
mixing of said powder; and then
direct compression of the mixture obtained as a colouring solid particle; and then
spraying of a coating composition onto the solid particles obtained previously.

The milling step may notably be performed using a mill, for instance a U5 Quadro® Comil®.

The screening step may notably be performed using a granulator, for instance a Roto P50 (Zanchetta) or High Shear Mixer P/VAC-10 (Diosna).

The mixing step may notably be performed using a blender, for instance an MB015 Blender (Pharmatech).

The step of direct compression of the mixture may notably be performed using a compression table, for instance a PR-1500 (PTK).

The step of coating said particles may notably be performed using a film-coating station, for instance an LDCS-Pilot Hi-Coater® (Freund-vector).

The coating composition for coating the solid particles according to the invention comprises one or more cellulose ethers as described previously for the upper coating layer.

Preferably, said coating composition also comprises one or more of the preferred ingredients of the upper coating layer as described previously; more preferentially in contents as described previously in the upper coating layer.

More preferentially, said coating composition also comprises one or more solvents chosen from water, $C_1$-$C_6$ alcohols, and mixtures thereof; even more preferentially chosen from water, ethanol, and mixtures thereof.

By way of example, the coating composition may be prepared from one or more solvents, in particular as described above, and from a mixture containing hydroxypropylmethylcellulose and hydroxypropylcellulose. According to this example, the coating composition may optionally contain one or more fatty substances, which are preferably liquid at 25° C. and at atmospheric pressure, such as one or more fatty alcohols, fatty esters and/or triglycerides, for example chosen from octyldodecanol, isopropyl myristate, a plant oil and/or caprylic/capric acid triglyceride.

The composition may also optionally contain talc and/or pigments for colouring the coating, preferably talc and pigments such as titanium dioxide.

According to another particular preparation method, the solid particles according to the invention may be prepared via wet granulation according to the following steps:
- premixing the binder(s) (for example lactose, microcrystalline cellulose, polyvinyl alcohol (PVA)), and the direct dye(s) and/or the oxidation dye precursor(s); and then
- spraying onto the premix the disintegrant(s) (for example a crosslinked polyvinylpyrrolidone) dissolved in one or more solvents such as those described in the above paragraph for the coating composition, in particular in water, for the production of the desired granulate; and then
- drying of the granulate; and then
- milling of the other ingredients of the solid particle; and then
- screening of the powder obtained by milling and of the granulate; and then
- mixing of the powders obtained by screening; and then
- direct compression of the mixture obtained as a solid particle; and optionally
- coating of the solid particles obtained.

More particularly, it has been observed that the solid particles obtained by a direct compression process exhibit better dissolution (faster and easier) in an aqueous composition than the particles obtained by extrusion process.

Indeed, the particles obtained by an extrusion process are denser than those obtained by direct compression. Therefore, the particles obtained by an extrusion process take longer to dissolve in an aqueous composition than the particles obtained by direct compression, which is not particularly advantageous.

The process for preparing the particles according to the invention is advantageously a process by direct compression.

In addition, a process by direct compression exhibits better repeatability and reproducibility in the production of said particles according to the invention than an extrusion process.

Process for Preparing an Aqueous Dye Composition M

A subject of the present application is also a process for preparing an aqueous dye composition M, comprising the mixing of one or more colouring solid particles as described previously with at least one aqueous composition A.

Preferably, said aqueous composition(s) A are chosen from an oxidizing aqueous composition A1 comprising one or more chemical oxidizing agents, and/or an alkaline aqueous composition A2 comprising one or more alkaline agents, preferably arginine, and/or an aqueous composition A3 comprising one or more thickening polymers.

Said aqueous compositions A1, A2 and A3 may or may not be different from each other. Preferably, said aqueous compositions A1, A2 and A3 are different from each other.

Aqueous Oxidizing Composition A1:

The process for preparing an aqueous dye composition M according to the invention may use an aqueous oxidizing composition A1 comprising one or more chemical oxidizing agents.

Preferably, the water content of the aqueous oxidizing composition A1 is between 30% and 99% by weight, more preferentially between 50% and 99% by weight, even better still between 50% and 90% by weight relative to the total weight of the aqueous oxidizing composition A1.

Chemical Oxidizing Agents

The aqueous oxidizing composition A1 comprises at least one chemical oxidizing agent.

For the purposes of the present invention, the term "chemical oxidizing agent" means an oxidizing agent other than atmospheric oxygen.

The chemical oxidizing agent(s) (or decolourizing agents) that may be used in the present invention may be chosen from hydrogen peroxide, urea peroxide, alkali metal bromates, persalts such as perborates and persulfates, in particular sodium persulfate, potassium persulfate and ammonium persulfate, peracids and oxidase enzymes (with the optional cofactors thereof), among which mention may be made of peroxidases, 2-electron oxidoreductases such as uricases and 4-electron oxygenases such as laccases, and mixtures thereof; more preferentially, the chemical oxidizing agent(s) are chosen from hydrogen peroxide, persalts, and mixtures thereof.

Preferably, when composition A1 is used in the preparation process according to the invention, the total content of chemical oxidizing agent(s) present in the aqueous oxidizing composition A1 is between 0.1% and 35% by weight, more preferentially between 0.1% and 30% by weight, even more preferentially between 0.5% and 25% by weight and better still between 2% and 12% by weight, relative to the total weight of the aqueous oxidizing composition A1.

Aqueous Alkaline Composition A2

The process for preparing an aqueous dye composition M according to the invention may use an aqueous alkaline composition A2 comprising one or more alkaline agents.

Preferably, the alkaline composition A2 comprises arginine.

Preferably, the water content of the aqueous alkaline composition A2 is between 30% and 99% by weight, more preferentially between 50% and 99% by weight, better still between 50% and 90% by weight relative to the total weight of the aqueous alkaline composition A2.

When the alkaline composition A2 comprises arginine, the arginine content is preferably between 0.05% and 25% by weight, more preferentially between 0.1% and 15% by weight, even more preferentially between 0.5% and 10% by weight, or even between 1% and 5% by weight, relative to the total weight of the aqueous alkaline composition A2.

The aqueous alkaline composition A2 according to the invention may comprise at least one alkaline agent other than arginine.

The Alkaline Agents Other than Arginine

The aqueous alkaline composition A2 may comprise at least one additional alkaline agent other than arginine.

Preferably, the alkaline agent(s) other than arginine may be chosen from organic alkaline agents and inorganic alkaline agents.

Preferably, the organic alkaline agent(s) are chosen from organic amines, the $pK_b$ of which at 25° C. is less than 12, more preferentially less than 10 and even more advantageously less than 6. It should be noted that it is the $pK_b$ corresponding to the function which has the highest basicity.

In addition, the organic amines do not comprise any alkyl or alkenyl fatty chains comprising more than ten carbon atoms.

The organic alkaline agent(s) are preferably chosen from alkanolamines such as monoalkanolamines, dialkanolamines or trialkanolamines comprising from one to three identical or different $C_1$-$C_4$ hydroxyalkyl radicals.

The term "alkanolamine" means an organic amine comprising a primary, secondary or tertiary amine function, and one or more linear or branched $C_1$ to $C_8$ alkyl groups bearing one or more hydroxyl radicals.

Alkanolamines chosen from monoethanolamine (MEA), diethanolamine, triethanolamine, monoisopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethyl) aminomethane are in particular suitable for performing the invention. Among the alkanolamines, it is most particularly preferred to use monoethanolamine.

The amino acids other than arginine that may be used are of natural or synthetic origin, in their L, D or racemic form, and include at least one acid function chosen more particularly from carboxylic acid, sulfonic acid, phosphonic acid and phosphoric acid functions. The amino acids may be in neutral or ionic form.

As amino acids other than arginine that may be used in the present invention, mention may notably be made of aspartic acid, glutamic acid, alanine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids other than arginine are basic amino acids comprising an additional amine function optionally included in a ring or in a ureido function.

The organic amine may also be chosen from organic amines of heterocyclic type. Besides histidine that has already been mentioned in the amino acids, mention may in particular be made of pyridine, piperidine, imidazole, triazole, tetrazole and benzimidazole.

The organic amine may also be chosen from amino acid dipeptides. As amino acid dipeptides that may be used in the present invention, mention may be made notably of carnosine, anserine and balenine.

The organic amine may also be chosen from compounds including a guanidine function. As amines of this type that may be used in the present invention, mention may notably be made of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-([amino(imino)methyl]amino)ethane-1-sulfonic acid.

Among the additional inorganic alkaline agents that may be used in the process according to the invention, mention may be made of mineral hydroxides.

The mineral hydroxides may be chosen from alkali metal, alkaline-earth metal, transition metal and ammonium hydroxides. Examples of mineral hydroxides that may be mentioned include ammonium hydroxide, sodium hydroxide, lithium hydroxide, calcium hydroxide, magnesium hydroxide, barium hydroxide, strontium hydroxide, manganese hydroxide and zinc hydroxide.

Among the mineral hydroxides, ammonium hydroxide, also known as aqueous ammonia, is preferred.

The inorganic alkaline agent(s) may also be chosen from urea, ammonium salts such as ammonium chloride, ammonium sulfate, ammonium phosphate or ammonium nitrate, and silicates, phosphates or carbonates of alkali metals or alkaline-earth metals, such as lithium, sodium, potassium, magnesium, calcium and barium, and mixtures thereof, preferably from alkali metal or alkaline-earth metal silicates, in particular alkali metal or alkaline-earth metal metasilicates such as sodium metasilicate.

Preferably, the alkaline agent(s) other than arginine that are useful in the invention are chosen from aqueous ammonia, alkali metal or alkaline-earth metal metasilicates, alkanolamines, amino acids in neutral or ionic form, in particular basic amino acids, compounds including a guanidine function, and preferably from aqueous ammonia, alkali metal or alkaline-earth metal metasilicates and alkanolamines.

Preferably, the total content of alkaline agent(s) of the aqueous composition A2 ranges from 0.1% to 25% by weight, preferentially from 1% to 20% by weight and better still from 5% to 15% by weight.

According to a preferred embodiment of the invention, the alkaline aqueous composition A2 comprises arginine and one or more additional alkaline agents other than arginine; more preferentially one or more additional alkaline agents other than arginine chosen from aqueous ammonia, alkanolamines, alkali metal or alkaline-earth metal metasilicates, and mixtures thereof; even more preferentially from aqueous ammonia, monoethanolamine, sodium metasilicate, and mixtures thereof.

Preferably, when the aqueous alkaline composition A2 comprises arginine and one or more additional alkaline agents other than arginine, the additional alkaline agent(s) other than arginine represent a total content of between 0.05% and 25% by weight, more preferentially between 0.1% and 20% by weight, and even more preferentially between 0.5% and 15% by weight, relative to the total weight of the alkaline aqueous composition A2.

Advantageously, the pH of the alkaline aqueous composition A2 according to the invention generally ranges from 8 to 13, preferably from 9 to 12.5 and better still from 10 to 12.5.

Aqueous Composition A3

The process for preparing an aqueous dye composition M according to the invention may use an aqueous composition A3 comprising one or more thickening polymers.

Preferably, the water content of the aqueous composition A3 is between 30% and 99% by weight, more preferentially between 50% and 99% by weight and better still between 50% and 90% by weight, relative to the total weight of the aqueous composition A3.

Thickening Polymers

The aqueous composition A3 according to the invention comprises one or more thickening polymers.

Preferably, the thickening polymer(s) are chosen from associative polymers; more preferentially from anionic, nonionic, cationic or amphoteric associative polymers, and mixtures thereof; even more preferentially from anionic associative polymers and better still from acrylic anionic associative polymers.

It is recalled that "associative polymers" are polymers that are capable, in an aqueous medium, of reversibly associating with each other or with other molecules.

Their chemical structure more particularly comprises at least one hydrophilic zone and at least one hydrophobic zone.

The term "hydrophobic zone" means a radical or polymer with a saturated or unsaturated, linear or branched hydrocarbon-based chain, comprising at least 8 carbon atoms, preferably from 10 to 30 carbon atoms, in particular from 12 to 30 carbon atoms and more preferentially from 18 to 30 carbon atoms.

Preferentially, the hydrocarbon-based group is derived from a monofunctional compound. By way of example, the hydrophobic group may be derived from a fatty alcohol, for instance stearyl alcohol, dodecyl alcohol or decyl alcohol. It may also denote a hydrocarbon-based polymer, for instance polybutadiene.

For the purposes of the invention, the term "fatty alcohol" means a compound of formula R—OH with R denoting an optionally substituted saturated or unsaturated, linear or branched hydrocarbon-based chain, comprising at least 8 carbon atoms, preferably from 10 to 30 carbon atoms, in particular from 12 to 30 carbon atoms and more preferentially from 18 to 30 carbon atoms.

For the purposes of the invention, the term "fatty acid" means a compound of formula R—COOH with R denoting an optionally substituted saturated or unsaturated, linear or branched hydrocarbon-based chain, comprising at least 8 carbon atoms, preferably from 10 to 30 carbon atoms, in particular from 12 to 30 carbon atoms and more preferentially from 18 to 30 carbon atoms.

Among the associative polymers of anionic type that may be mentioned are:
(a) those including at least one hydrophilic unit and at least one fatty-chain allyl ether unit, more particularly those whose hydrophilic unit is formed by an ethylenic unsaturated anionic monomer, more particularly a vinylcarboxylic acid and most particularly an acrylic acid or a methacrylic acid or mixtures thereof.

Among these anionic associative polymers, the ones that are particularly preferred according to the invention are polymers formed from 20% to 60% by weight of acrylic acid and/or of methacrylic acid, from 5% to 60% by weight of lower alkyl (meth)acrylates, from 2% to 50% by weight of fatty-chain allyl ether, and from 0 to 1% by weight of a crosslinking agent which is a well-known copolymerizable unsaturated polyethylenic monomer, for instance diallyl phthalate, allyl (meth)acrylate, divinylbenzene, (poly)ethylene glycol dimethacrylate or methylenebisacrylamide.

Among the latter polymers, those most particularly preferred are crosslinked terpolymers of methacrylic acid, of ethyl acrylate and of polyethylene glycol (10 EO) stearyl alcohol ether (Steareth-10), notably those sold by the company Ciba under the names Salcare SC 80® and Salcare SC 90®, which are aqueous 30% emulsions of a crosslinked terpolymer of methacrylic acid, of ethyl acrylate and of steareth-10 allyl ether (40/50/10);
(b) those including i) at least one hydrophilic unit of unsaturated olefinic carboxylic acid type, and ii) at least one hydrophobic unit of the ($C_{10}$-$C_{30}$) alkyl ester of an unsaturated carboxylic acid type.

($C_{10}$-$C_{30}$) Alkyl esters of unsaturated carboxylic acids that are useful in the invention comprise, for example, lauryl acrylate, stearyl acrylate, decyl acrylate, isodecyl acrylate and dodecyl acrylate, and the corresponding methacrylates, lauryl methacrylate, stearyl methacrylate, decyl methacrylate, isodecyl methacrylate and dodecyl methacrylate.

Anionic polymers of this type are described and prepared, for example, according to patents U.S. Pat. Nos. 3,915,921 and 4,509,949.

Among the anionic associative polymers of this type that will be used more particularly are those constituted of from 95% to 60% by weight of acrylic acid (hydrophilic unit), 4% to 40% by weight of $C_{10}$-$C_{30}$ alkyl acrylate (hydrophobic unit) and 0 to 6% by weight of crosslinking polymerizable monomer, or alternatively those constituted of from 98% to 96% by weight of acrylic acid (hydrophilic unit), 1% to 4% by weight of $C_{10}$-$C_{30}$ alkyl acrylate (hydrophobic unit) and 0.1% to 0.6% by weight of crosslinking polymerizable monomer such as those described previously.

Among said polymers above, the ones most particularly preferred according to the present invention are the products sold by the company Goodrich under the trade names Pemulen TR1®, Pemulen TR2®, Carbopol 1382®, and even more preferentially Pemulen TR1®, and the product sold by the company SEPPIC under the name Coatex SX®.

Mention may also be made of the acrylic acid/lauryl methacrylate/vinylpyrrolidone terpolymer sold under the name Acrylidone LM by the company ISP.
(c) maleic anhydride/$C_{30}$-$C_{38}$ α-olefin/alkyl maleate terpolymers, such as the product (maleic anhydride/$C_{30}$-$C_{38}$ α-olefin/isopropyl maleate copolymer) sold under the name Performa V 1608® by the company Newphase Technologies.
(d) acrylic terpolymers comprising:
  i) about 20% to 70% by weight of an α,β-monoethylenically unsaturated carboxylic acid [A],
  ii) about 20% to 80% by weight of an α,β-monoethylenically unsaturated non-surfactant monomer other than [A],
  iii) about 0.5% to 60% by weight of a nonionic monourethane which is the product of reaction of a monohydric surfactant with a monoethylenically unsaturated monoisocyanate, such as those described in patent application EP-A-0 173 109 and more particularly the terpolymer described in Example 3, namely a methacrylic acid/methyl acrylate/behenyl alcohol dimethyl-meta-isopropenylbenzylisocyanate ethoxylated (40 OE) terpolymer, as an aqueous 25% dispersion.
(e) copolymers including among their monomers an α,β-monoethylenically unsaturated carboxylic acid and an ester of an α,β-monoethylenically unsaturated carboxylic acid and of an oxyalkylenated fatty alcohol.

Preferentially, these compounds also comprise as monomer an ester of an α,β-monoethylenically unsaturated carboxylic acid and of a $C_1$-$C_4$ alcohol.

As examples of compounds of this type, mention may be made of Aculyn 22® (INCI name: Acrylates/steareth-20 methacrylate copolymer) sold by the company Röhm & Haas, which is a methacrylic acid/ethyl acrylate/stearyl methacrylate oxyalkylenated terpolymer, and also Aculyn 88 (INCI name: Acrylates/steareth-20 methacrylate crosspolymer) or Aculyn 28 (INCI name: Acrylates/beheneth-25 methacrylate copolymer) also sold by the company Röhm & Haas.
(f) amphiphilic polymers including at least one ethylenically unsaturated monomer bearing a sulfonic group, in free or partially or totally neutralized form and comprising at least one hydrophobic part. These polymers may be crosslinked or non-crosslinked. They are preferably crosslinked.

The ethylenically unsaturated monomers bearing a sulfonic group are notably chosen from vinylsulfonic acid, styrenesulfonic acid, (meth)acrylamido($C_1$-$C_{22}$)alkylsulfonic acids, N—($C_1$-$C_{22}$)alkyl(meth)acrylamido($C_1$-$C_{22}$)alkylsulfonic acids such as undecylacrylamidomethanesulfonic acid, and also partially or totally neutralized forms thereof.

(Meth)acrylamido($C_1$-$C_{22}$)alkylsulfonic acids, for instance acrylamidomethanesulfonic acid, acrylamidoethanesulfonic acid, acrylamidopropanesulfonic acid, 2-acrylamido-2-methylpropanesulfonic acid, methacrylamido-2-methylpropanesulfonic acid, 2-acrylamido-n-butanesulfonic acid, 2-acrylamido-2,4,4-trimethylpentanesulfonic acid, 2-methacrylamidododecylsulfonic acid or 2-acrylamido-2,6-dimethyl-3-heptanesulfonic acid, and also partially or totally neutralized forms thereof, will more preferentially be used.

2-Acrylamido-2-methylpropanesulfonic acid (AMPS), and also partially or totally neutralized forms thereof, will more particularly be used.

The polymers of this family may be chosen notably from random amphiphilic AMPS polymers modified by reaction with a $C_6$-$C_{22}$ n-monoalkylamine or di-n-alkylamine, and such as those described in patent application WO 00/31154 (forming an integral part of the content of the description). These polymers may also contain other ethylenically unsaturated hydrophilic monomers chosen, for example, from (meth)acrylic acids, β-substituted alkyl derivatives thereof or esters thereof obtained with monoalcohols or mono- or polyalkylene glycols, (meth)acrylamides, vinylpyrrolidone, maleic anhydride, itaconic acid or maleic acid, or mixtures of these compounds.

The preferred polymers of this family are chosen from amphiphilic copolymers of AMPS and of at least one ethylenically unsaturated hydrophobic monomer.

These same copolymers may also contain one or more ethylenically unsaturated monomers not including a fatty chain, such as (meth)acrylic acids, 0-substituted alkyl derivatives thereof or esters thereof obtained with monoalcohols or mono- or polyalkylene glycols, (meth)acrylamides, vinylpyrrolidone, maleic anhydride, itaconic acid or maleic acid, or mixtures of these compounds.

These copolymers are described notably in patent application EP-A 750 899, patent U.S. Pat. No. 5,089,578 and in the following publications from Yotaro Morishima:

Self-assembling amphiphilic polyelectrolytes and their nanostructures, Chinese Journal of Polymer Science, Vol. 18, No. 40, (2000), 323-336;

Micelle formation of random copolymers of sodium 2-(acrylamido)-2-methylpropanesulfonate and a nonionic surfactant macromonomer in water as studied by fluorescence and dynamic light scattering—Macromolecules, Vol. 33, No. 10 (2000), 3694-3704;

Solution properties of micelle networks formed by nonionic moieties covalently bound to a polyelectrolyte: salt effects on rheological behavior—Langmuir, Vol. 16, No. 12, (2000), 5324-5332;

Stimuli responsive amphiphilic copolymers of sodium 2-(acrylamido)-2-methylpropanesulfonate and associative macromonomers, Polym. Preprint, Div. Polym. Chem., 40(2), (1999), 220-221.

Among these polymers, mention may be made of:

crosslinked or non-crosslinked, neutralized or non-neutralized copolymers, including from 15% to 60% by weight of AMPS units and from 40% to 85% by weight of ($C_5$-$C_{16}$)alkyl(meth)acrylamide or ($C_5$-$C_{16}$)alkyl (meth)acrylate units relative to the polymer, such as those described in patent application EP-A 750 899;

terpolymers including from 10 mol % to 90 mol % of acrylamide units, from 0.1 mol % to 10 mol % of AMPS units and from 5 mol % to 80 mol % of n-($C_6$-$C_{18}$)alkylacrylamide units, such as those described in U.S. Pat. No. 5,089,578.

Mention may also be made of copolymers of totally neutralized AMPS and of dodecyl methacrylate, and also crosslinked and non-crosslinked copolymers of AMPS and of n-dodecylmethacrylamide, such as those described in the Morishima articles mentioned above.

Among the cationic associative polymers, mention may be made of:

(a) cationic associative polyurethanes;

(b) the compound sold by the company Noveon under the name Aqua CC and which corresponds to the INCI name Polyacrylate-1 Crosspolymer.

Polyacrylate-1 Crosspolymer is the product of polymerization of a monomer mixture comprising:

a di($C_1$-$C_4$ alkyl)amino($C_1$-$C_6$ alkyl) methacrylate, one or more $C_1$-$C_{30}$ alkyl esters of (meth)acrylic acid, a polyethoxylated $C_{10}$-$C_{30}$ alkyl methacrylate (20-25 mol of ethylene oxide units), a 30/5 polyethylene glycol/polypropylene glycol allyl ether, a hydroxy($C_2$-$C_6$ alkyl) methacrylate, and an ethylene glycol dimethacrylate.

(c) quaternized (poly)hydroxyethylcelluloses modified with groups including at least one fatty chain, such as alkyl, arylalkyl or alkylaryl groups including at least 8 carbon atoms, or mixtures thereof. The alkyl radicals borne by the above quaternized celluloses or hydroxyethylcelluloses preferably include from 8 to 30 carbon atoms. The aryl radicals preferably denote phenyl, benzyl, naphthyl or anthryl groups. Examples of quaternized alkylhydroxyethylcelluloses containing $C_8$-$C_{30}$ fatty chains that may be indicated include the products Quatrisoft LM 200®, Quatrisoft LM-X 529-18-A®, Quatrisoft LM-X 529-18-B® ($C_{12}$ alkyl) and Quatrisoft LM-X 529-8® ($C_{18}$ alkyl) sold by the company Aqualon, and the products Crodacel QM®, Crodacel QL® ($C_{12}$ alkyl) and Crodacel QS® ($C_{18}$ alkyl) sold by the company Croda and the product Softcat SL 100® sold by the company Aqualon.

(d) cationic polyvinyllactam polymers.

Such polymers are described, for example, in patent application WO-00/68282.

As cationic poly(vinyllactam) polymers according to the invention, vinylpyrrolidone/dimethylaminopropylmethacrylamide/dodecyldimethylmethacrylam idopropylammonium tosylate terpolymers, vinylpyrrolidone/dimethylaminopropylmethacrylamide/cocoyldimethylmethacrylami dopropylammonium tosylate terpolymers, vinylpyrrolidone/dimethylaminopropylmethacrylamide/ lauryldimethylmethacrylamid opropylammonium tosylate or chloride terpolymers are notably used.

The amphoteric associative polymers are preferably chosen from those including at least one noncyclic cationic unit. Even more particularly, those prepared from or comprising 1 to 20 mol %, preferably 1.5 to 15 mol % and even more particularly 1.5 to 6 mol % of fatty-chain monomer relative to the total number of moles of monomers are preferred.

Amphoteric associative polymers according to the invention are described and prepared, for example, in patent application WO 98/44012.

Among the amphoteric associative polymers according to the invention, the ones that are preferred are acrylic acid/(meth)acrylamidopropyltrimethylammonium chloride/ stearyl methacrylate terpolymers.

The associative polymers of nonionic type that may be used according to the invention are preferably chosen from:

(a) copolymers of vinylpyrrolidone and of fatty-chain hydrophobic monomers, of which examples that may be mentioned include:

the products Antaron V216® or Ganex V216® (vinylpyrrolidone/hexadecene copolymer), sold by the company ISP;

the products Antaron V220® or Ganex V220® (vinylpyrrolidone/eicosene copolymer), sold by the company ISP;

(b) copolymers of $C_1$-$C_6$ alkyl methacrylates or acrylates and of amphiphilic monomers including at least one fatty chain, for instance the oxyethylenated methyl acrylate/stearyl acrylate copolymer sold by the company Goldschmidt under the name Antil 208®;

(c) copolymers of hydrophilic methacrylates or acrylates and of hydrophobic monomers including at least one fatty chain, for instance the polyethylene glycol methacrylate/lauryl methacrylate copolymer;

(d) polyurethane polyethers including in their chain both hydrophilic blocks usually of polyoxyethylenated nature and hydrophobic blocks, which may be aliphatic sequences alone and/or cycloaliphatic and/or aromatic sequences;

(e) polymers with an aminoplast ether backbone containing at least one fatty chain, such as the Pure Thix® compounds sold by the company Sud-Chemie;

(f) celluloses or derivatives thereof, modified with groups including at least one fatty chain, such as alkyl, arylalkyl or alkylaryl groups or mixtures thereof in which the alkyl groups are of $C_8$, and in particular:

nonionic alkylhydroxyethylcelluloses such as the products Natrosol Plus Grade 330 CS and Polysurf 67 ($C_{16}$ alkyl) sold by the company Aqualon;

nonionic nonoxynylhydroxyethylcelluloses such as the product Amercell HM-1500 sold by the company Amerchol;

nonionic alkylcelluloses such as the product Bermocoll EHM 100 sold by the company Berol Nobel;

(g) associative guar derivatives, for instance hydroxypropyl guars modified with a fatty chain, such as the product Esaflor HM 22 (modified with a $C_{22}$ alkyl chain) sold by the company Lamberti; the product Miracare XC 95-3 (modified with a $C_{14}$ alkyl chain) and the product RE 205-146 (modified with a $C_{20}$ alkyl chain) sold by Rhodia Chimie.

Preferably, the polyurethane polyethers include at least two hydrocarbon-based lipophilic chains containing from 6 to 30 carbon atoms, separated by a hydrophilic block, the hydrocarbon-based chains possibly being side chains or chains at the end of the hydrophilic block. In particular, it is possible for one or more side chains to be envisaged. In addition, the polymer may include a hydrocarbon-based chain at one end or at both ends of a hydrophilic block.

The polyurethane polyethers may be multiblock, in particular in triblock form. The hydrophobic blocks may be at each end of the chain (for example: triblock copolymer bearing a hydrophilic central block) or distributed both at the ends and in the chain (for example, multiblock copolymer). These same polymers may also be graft polymers or starburst polymers.

The nonionic fatty-chain polyurethane polyethers may be triblock copolymers, the hydrophilic block of which is a polyoxyethylene chain including from 50 to 1000 oxyethylene groups. The nonionic polyurethane polyethers include a urethane bond between the hydrophilic blocks, whence the origin of the name.

By extension, also included among the nonionic fatty-chain polyurethane polyethers are those in which the hydrophilic blocks are linked to the lipophilic blocks via other chemical bonds.

As examples of nonionic fatty-chain polyurethane polyethers that may be used in the invention, use may also be made of Rheolate 205® bearing a urea function, sold by the company Rheox, or Rheolate® 208, 204 or 212, and also Acrysol RM 184®.

Mention may also be made of the product Elfacos T210® bearing a $C_{12}$-$C_{14}$ alkyl chain, and the product Elfacos T212® bearing a $C_{18}$ alkyl chain, from Akzo.

The product DW 1206B® from Röhm & Haas bearing a $C_{20}$ alkyl chain and a urethane bond, sold at a solids content of 20% in water, may also be used.

Use may also be made of solutions or dispersions of these polymers, notably in water or in aqueous-alcoholic medium. Examples of such polymers that may be mentioned include Rheolate® 255, Rheolate® 278 and Rheolate® 244 sold by the company Rheox. Use may also be made of the products DW 1206F and DW 1206J sold by the company Röhm & Haas.

The polyurethane polyethers that may be used according to the invention are in particular those described in the article by G. Fonnum, J. Bakke and Fk. Hansen—*Colloid Polym. Sci.*, 271, 380-389 (1993).

It is even more particularly preferred to use a polyurethane polyether that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane polyethers are notably sold by the company Röhm & Haas under the names Aculyn 46® and Aculyn 44® [Aculyn 46® is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%); Aculyn 44® is a polycondensate of polyethylene glycol containing 150 or 180 mol of ethylene oxide, of decyl alcohol and of methylenebis(4-cyclohexyl isocyanate) (SMDI), at 35% by weight in a mixture of propylene glycol (39%) and water (26%)].

Advantageously, the associative polymer(s) are chosen from associative polymers bearing acrylic and/or methacrylic units, and polymers bearing 2-acrylamido-2-methylpropanesulfonic acid units and/or the salified form thereof.

According to a preferred embodiment of the invention, the thickening polymer(s) are chosen from associative polymers; more preferentially from anionic associative polymers; even more preferentially from acrylic anionic associative polymers; better still from acrylic anionic associative polymers of the type (a), (b), (d) and (e) as described previously; even better still from copolymers including among their monomers an α,β-monoethylenically unsaturated carboxylic acid and an ester of an α,β-monoethylenically unsaturated carboxylic acid and of an oxyalkylenated fatty alcohol.

Preferably, the content of thickening polymer(s) present in the aqueous composition A3 is between 0.01% and 15% by weight, more preferentially between 0.05% and 10% by weight and even more preferentially between 0.1% and 5% by weight, relative to the total weight of the aqueous composition A3.

Preferably, when one or more associative polymers are present in the aqueous composition A3, the total content of associative polymer(s) is between 0.01% and 10% by weight, more preferentially between 0.05% and 5% by weight, even more preferentially between 0.1% and 2% by weight, relative to the total weight of the aqueous composition A3.

The aqueous composition(s) A used in the preparation process according to the present invention may optionally also comprise one or more additives such as nacres; fatty substances; cationic polymers other than the thickening polymers and notably the associative polymers described previously; vitamins or provitamins; surfactants, notably nonionic surfactants; pH stabilizers; preserving agents; fragrances.

A person skilled in the art will take care to select the optional additives and the amount thereof so that they do not harm the properties of the processes and compositions of the present invention.

These additives, when they are present, are generally present in the aqueous composition(s) A in an amount ranging from 0 to 20% by weight relative, respectively, to the total weight of the aqueous composition containing same.

The aqueous composition(s) A used in the preparation process according to the present invention may optionally also comprise one or more organic solvents.

Examples of organic solvents that may be mentioned include linear or branched $C_2$ to $C_4$ alkanols, such as ethanol and isopropanol; glycerol; polyols and polyol ethers, for instance 2-butoxyethanol, propylene glycol, hexylene glycol, dipropylene glycol, propylene glycol monomethyl ether, diethylene glycol monomethyl ether and monoethyl ether, and also aromatic alcohols or ethers, such as benzyl alcohol or phenoxyethanol, and mixtures thereof.

Advantageously, the preparation process according to the invention comprises the mixing of an aqueous composition A with a number N of colouring solid particles when said particles are identical, or several numbers $N_x$, which may be identical or different, when the colouring solid particles are different. Said solid particles have a volume of between 25 $mm^3$ and 125 $mm^3$.

N is an integer greater than or equal to 2;
and $N_x$ are integers greater than or equal to 1, and x is an index ranging from 1 to n with n being the number of colouring solid particles of different types.
N and $N_x$ are defined before the use of the aqueous dye composition M, as a function of the shade desired by the user and/or of the user's specificities such as the pre-existing shade and/or the nature of the keratin fibres.

Preferably, the numbers N and $N_x$ are defined by means of computer software.

According to a preferred embodiment of the invention, the process for preparing an aqueous dye composition M comprises the mixing of:
one or more solid particles of a first type P1, having a volume of between 25 $mm^3$ and 125 $mm^3$, and containing only one oxidation dye precursor $C_1$; and
one or more solid particles of a second type P2, having a volume of between 25 $mm^3$ and 125 $mm^3$, and containing only one oxidation dye precursor $C_2$; with
at least one aqueous composition A as described previously;
it being understood that the oxidation dye precursor $C_1$ is different from the oxidation dye precursor $C_2$.

The oxidation dye precursors $C_1$ and $C_2$ are preferably chosen from the oxidation dye precursors as described previously.

More preferentially, the preparation process according to the invention comprises the mixing of a number $N_1$ of colouring solid particle(s) of a first type P1 as described previously with a number $N_2$ of colouring solid particles(s) of a second type P2 as described previously, $N_1$ and $N_2$ being integers greater than or equal to 1 defined before the use of the dye composition M, as a function of the shade desired by the user and/or of the user's specificities such as the pre-existing shade and/or the nature of the keratin fibres.

Even more preferentially, the numbers $N_1$ and $N_2$ are defined by means of computer software.

Preferably, the preparation process according to the invention is performed less than 2 hours, more preferentially less than 1 hour and even more preferentially less than 30 minutes before the application of said dye composition M to the keratin fibres.

According to another preferred embodiment of the invention, the process for preparing an aqueous composition M for dyeing keratin fibres, in particular human keratin fibres such as the hair, comprises:
a) a step of mixing:
(i) one or more identical or different solid particles having a volume of between 25 $mm^3$ and 125 $mm^3$, each containing one or more oxidation dye precursors, as described previously, with
(ii) an oxidizing aqueous composition A1 comprising one or more chemical oxidizing agents, preferably chosen from those described previously, more preferentially from hydrogen peroxide, persalts and mixtures thereof; and then
a') optionally a step of mixing the composition obtained following said step a) with an aqueous composition A3 comprising at least one thickening polymer, preferably chosen from associative polymers, more preferentially chosen from the associative polymers as described previously, even more preferentially from the anionic associative polymers as described previously and notably acrylic anionic associative polymers such as copolymers including among their monomers an α,β-monoethylenically unsaturated carboxylic acid and an ester of an α,β-monoethylenically unsaturated carboxylic acid and of an oxyalkylenated fatty alcohol; and then
b) a step of mixing the composition obtained previously with an alkaline aqueous composition A2 comprising arginine and optionally one or more additional alkaline agents other than arginine, as described previously.

Preferably according to this embodiment, the total content of chemical oxidizing agent(s) present in the oxidizing aqueous composition A1 is between 0.1% and 35% by weight, more preferentially between 0.1% and 30% by weight, even more preferentially between 0.5% and 25% by weight, even better still between 2% and 12% by weight, relative to the total weight of the oxidizing aqueous composition A1.

Preferably according to this embodiment, the content of arginine present in the alkaline aqueous composition A2 is between 0.05% and 25% by weight, more preferentially between 0.1% and 15% by weight, even more preferentially between 0.5% and 10% by weight, better still between 1% and 5% by weight, relative to the total weight of the alkaline aqueous composition A2.

Preferably according to this embodiment, when the additional alkaline agent(s) other than arginine are present in the alkaline aqueous composition A2, the total content of additional alkaline agent(s) other than arginine is between 0.05% and 25% by weight, more preferentially between 0.1% and 20% by weight, and even more preferentially between 0.5% and 15% by weight, relative to the total weight of the alkaline aqueous composition A2.

Preferably according to this embodiment, when the aqueous composition A3 is added, the total content of thickening polymer(s), and more preferentially of associative polymer (s), present in the aqueous composition A3 is between 0.01% and 10% by weight, more preferentially between 0.05% and 5% by weight and even more preferentially between 0.1% and 2% by weight, relative to the total weight of the aqueous composition A3.

According to yet another preferred embodiment of the invention, the process for preparing a composition for dyeing keratin fibres, in particular human keratin fibres such as the hair, comprises:

a) a step of mixing:
  (i) one or more solid particles of the type P1 and one or more solid particles of the type P2, as described previously, with
  (ii) an oxidizing aqueous composition A1 comprising one or more chemical oxidizing agents, preferably chosen from those described previously, more preferentially from hydrogen peroxide, persalts and mixtures thereof; and then
a') optionally a step of mixing the composition obtained following said step a) with an aqueous composition A3 comprising at least one thickening polymer, preferably chosen from associative polymers, more preferentially chosen from the associative polymers as described previously, even more preferentially from the anionic associative polymers as described previously and notably acrylic anionic associative polymers such as copolymers including among their monomers an α,β-monoethylenically unsaturated carboxylic acid and an ester of an α,β-monoethylenically unsaturated carboxylic acid and of an oxyalkylenated fatty alcohol; and then
b) a step of mixing the composition obtained previously with an alkaline aqueous composition A2 comprising arginine and optionally one or more additional alkaline agents other than arginine, as described previously.

Preferably according to this embodiment, the total content of chemical oxidizing agent(s) present in the oxidizing aqueous composition A1 is between 0.1% and 35% by weight, more preferentially between 0.1% and 30% by weight, even more preferentially between 0.5% and 25% by weight, better still between 2% and 12% by weight, relative to the total weight of the oxidizing aqueous composition A1.

Preferably according to this embodiment, the content of arginine present in the alkaline aqueous composition A2 is between 0.05% and 25% by weight, more preferentially between 0.1% and 15% by weight, even more preferentially between 0.5% and 10% by weight, better still between 1% and 5% by weight, relative to the total weight of the alkaline aqueous composition A2.

Preferably according to this embodiment, when the additional alkaline agent(s) other than arginine are present in the alkaline aqueous composition A2, the total content of additional alkaline agent(s) other than arginine is between 0.05% and 25% by weight, more preferentially between 0.1% and 20% by weight, and even more preferentially between 0.5% and 15% by weight, relative to the total weight of the alkaline aqueous composition A2.

Preferably according to this embodiment, when the aqueous composition A3 is added, the total content of thickening polymer(s), and more preferentially of associative polymer(s), present in the aqueous composition A3 is between 0.01% and 10% by weight, more preferentially between 0.05% and 5% by weight and even more preferentially between 0.1% and 2% by weight, relative to the total weight of the aqueous composition A3.

According to another preferred embodiment of the process for preparing an aqueous composition M for dyeing keratin fibres, in particular human keratin fibres such as the hair, one or more colouring solid particles as described previously are at least mixed with an oxidizing aqueous composition A1 comprising one or more chemical oxidizing agents, and an aqueous composition A3 comprising at least one anionic associative polymer such as copolymers including among their monomers an α,β-monoethylenically unsaturated carboxylic acid and an ester of an α,β-monoethylenically unsaturated carboxylic acid and of an oxyalkylenated fatty alcohol, more preferentially the acrylates/beheneth-25 methacrylate copolymer.

The various mixtures of the preparation processes as described previously may be prepared using a mechanical stirrer, a magnetic stirrer, and/or by hand, for example using a colouring brush.

For the purposes of the invention, it is understood that the process for preparing an aqueous dye composition M according to the invention comprises the dissolution of said solid particle(s) in at least one aqueous composition A.

According to one embodiment of the invention, the process for preparing the dye composition M may also use one or more solid particles comprising a dye-free core, and an upper coating layer containing one or more cellulose ethers as described previously and covering said core, preferably totally.

The Dye Composition M

The dye composition M, or ready-to-use composition or final composition, is obtained after performing the preparation process according to the invention.

Preferably, the water content of said dye composition M is between 30% and 99% by weight, more preferentially between 50% and 99% by weight and better still between 50% and 90% by weight, relative to the total weight of said dye composition M.

Preferably, the content of arginine present in said dye composition M ranges from 0.001% to 20% by weight, more preferentially from 0.05% to 10% by weight, even more preferentially from 0.1% to 5% by weight and even better still from 0.5% to 3% by weight relative to the total weight of said dye composition M.

Preferably, the total content of alkaline agent(s) present in said dye composition M ranges from 0.001% to 30% by weight, more preferentially from 0.05% to 20% by weight, even more preferentially from 0.5% to 10% by weight and better still from 1% to 5% by weight, relative to the total weight of said dye composition M.

Preferably, the total content of chemical oxidizing agent(s) present in said dye composition M ranges from 0.001% to 30% by weight, more preferentially from 0.05% to 20% by weight, even more preferentially from 0.1% to 15% by weight and better still from 1% to 10% by weight relative to the total weight of said dye composition M.

Preferably, the total content of thickening polymer(s), more preferentially of associative polymer(s), present in said dye composition M ranges from 0.001% to 8% by weight, more preferentially from 0.005% to 4% by weight and even more preferentially from 0.01% to 1% by weight relative to the total weight of said dye composition M.

Preferably, the weight ratio of the total mass of the dye composition M, on the one hand, to the total mass of solid particles, on the other hand, is between 1 and 22, more preferentially between 2 and 15; even more preferentially between 5 and 12.

The dye composition M may be in various forms, such as in the form of liquids, creams or gels, or in any other form that is suitable for dyeing keratin fibres, and notably human hair.

A subject of the invention is also a process for dyeing keratin fibres, in particular human keratin fibres such as the hair, comprising:
- at least one step of preparing an aqueous dye composition M for dyeing keratin fibres according to the preparation process described previously; and then
- at least one step of applying said aqueous dye composition M to said keratin fibres.

Preferably, the preparation of said aqueous dye composition M for dyeing keratin fibres is performed less than 2 hours, more preferentially less than 1 hour and even more preferentially less than 30 minutes before the application of said aqueous dye composition M to the keratin fibres.

A subject of the invention is also the use of said aqueous dye composition M as obtained according to the preparation process according to the invention, for dyeing keratin fibres, in particular human keratin fibres such as the hair.

The examples that follow serve to illustrate the invention without, however, being limiting in nature.

EXAMPLES

The solid particles and the compositions below according to the present invention were prepared using the ingredients of which the contents, expressed as mass percentages of active material relative to the total weight of the solid particle or of the composition, are indicated in the tables below.

Examples of Particles
Solid Particle without an Upper Coating Layer

TABLE 1

| Ingredients | Amount |
| --- | --- |
| Microcrystalline cellulose | 56 |
| Lactose | 15 |
| PVP | 4.75 |
| Magnesium stearate | 2 |
| Silica | 1 |
| Toluene-2,5-diamine sulfate | 20 |
| Sodium sulfite | 1 |
| Water | 0.25 |

Example of Upper Coating Layer

TABLE 2

| Ingredients | Amount |
| --- | --- |
| Hydroxypropylmethylcellulose (HPMC) | 45 to 55 |
| Hydroxypropylcellulose (HPC) | 5 to 20 |
| Capric/caprylic triglyceride | 1 to 10 |
| Talc | qs 100 |
| Pigments | 0 to 40 |

Examples of Solid Particles with an Upper Coating Layer

TABLE 4

| Ingredients | Amount |
| --- | --- |
| Microcrystalline cellulose | 54.4 |
| Lactose | 14.6 |
| PVP | 4.6 |
| Magnesium stearate | 1.94 |
| Silica | 1.0 |
| Toluene-2,5-diamine sulfate | 19.4 |
| Sodium sulfite | 1.0 |
| Water | 0.2 |
| Hydroxypropylmethylcellulose | 1.46 |

TABLE 4-continued

| Ingredients | Amount |
| --- | --- |
| Hydroxypropylcellulose | 0.29 |
| Talc | 0.44 |
| Caprylic/capric triglyceride | 0.15 |
| Pigments | 0.51 |
| Alumina | 0.01 |

TABLE 5

| Ingredients | Amount |
| --- | --- |
| Microcrystalline cellulose | 77.2 |
| Lactose | 14.6 |
| PVP | 0.1 |
| Magnesium stearate | 1 |
| Silica | 0.54 |
| Resorcinol | 0.85 |
| Hydroxypropylmethylcellulose | 1.45 |
| Hydroxypropylcellulose | 0.30 |
| Talc | 0.4 |
| Caprylic/capric triglyceride | 0.15 |
| Pigments | 0.5 |
| Alumina | 0.01 |
| VP/VA copolymer | 2.9 |

TABLE 6

| Ingredients | Amount |
| --- | --- |
| Microcrystalline cellulose | 63.5 |
| Lactose | 9.7 |
| PVP | 0.1 |
| Magnesium stearate | 1 |
| Silica | 0.5 |
| Resorcinol | 16.5 |
| Ascorbic acid | 2.9 |
| Hydroxypropylmethylcellulose | 1.5 |
| Hydroxypropylcellulose | 0.3 |
| Talc | 0.44 |
| Caprylic/capric triglyceride | 0.15 |
| Pigments | 0.5 |
| Alumina | 0.01 |
| VP/VA copolymer | 2.9 |

TABLE 7

| Ingredients | Amount |
| --- | --- |
| Microcrystalline cellulose | 76.2 |
| Lactose | 15.5 |
| PVP | 0.5 |
| Magnesium stearate | 1.0 |
| Silica | 1.0 |
| 2,4-Diaminophenoxyethanol hydrochloride | 1.0 |
| Sodium metabisulfite | 1.94 |
| Water | 0.02 |
| Hydroxypropylmethylcellulose | 1.45 |
| Hydroxypropylcellulose | 0.29 |
| Talc | 0.44 |
| Caprylic/capric triglyceride | 0.15 |
| Pigments | 0.5 |
| Alumina | 0.01 |

TABLE 8

| Ingredients | Amount |
| --- | --- |
| Microcrystalline cellulose | 69.4 |
| Lactose | 11.6 |
| PVP | 2.8 |

TABLE 8-continued

| Ingredients | Amount |
| --- | --- |
| Magnesium stearate | 1.0 |
| Silica | 0.5 |
| m-Aminophenol | 7.8 |
| Sodium metabisulfite | 3.9 |
| Water | 0.15 |
| Hydroxypropylmethylcellulose | 1.46 |
| Hydroxypropylcellulose | 0.29 |
| Talc | 0.44 |
| Caprylic/capric triglyceride | 0.15 |
| Pigments | 0.5 |
| Alumina | 0.01 |

The volumes of the particles according to the invention in Tables 1 and 4 to 8 above are between 45 and 65 mm$^3$.

Oxidizing Composition

TABLE 9

| Ingredients | Amount (g) |
| --- | --- |
| Hydrogen peroxide | 12 |
| Stabilizer, sequestrant | qs |
| Phosphoric acid | qs pH = 2.2 ± 0.2 |
| Water | qs 100 |

Alkaline Composition 1

TABLE 10

| Ingredients | Amount |
| --- | --- |
| Arginine | 3 |
| Ammonium hydroxide | 2 |
| Monoethanolamine | 5.8 |
| Sodium metasilicate | 2 |
| Polyquaternium-6 | 2 |
| Hexadimethrine chloride | 1.2 |
| EDTA | 0.2 |
| Hydroxypropylmethylcellulose (HPMC) | 0.2 |
| Cetylhydroxyethylcellulose | 0.45 |
| PEG-40 stearate | 1.8 |
| Oleth-30 | 1.5 |
| Oleic acid | 3 |
| $C_{20}$-$C_{22}$ fatty alcohols | 3 |
| Stearamide MEA | 4.8 |
| Steareth-2 | 5.5 |
| Water | qs 100 |

Alkaline Composition 2

TABLE 11

| Ingredients | Amount |
| --- | --- |
| Arginine | 3 |
| Monoethanolamine | 5.8 |
| Sodium metasilicate | 2 |
| Polyquaternium-6 | 2 |
| Hexadimethrine chloride | 1.2 |
| EDTA | 0.2 |
| Hydroxypropylmethylcellulose (HPMC) | 1.2 |
| Cetylhydroxyethylcellulose | 0.45 |
| PEG-40 stearate | 1.8 |
| Oleth-30 | 1.5 |
| Oleic acid | 3 |
| $C_{20}$-$C_{22}$ fatty alcohols | 3 |
| Stearamide MEA | 4.8 |
| Steareth-2 | 5.5 |
| Water | qs 100 |

Thickening Composition

TABLE 12

| Ingredients | Amount |
| --- | --- |
| Hydrogen peroxide | 12 |
| Cetearyl alcohol | 8 |
| Acrylates/beheneth-25 methacrylate copolymer, under the reference Aculyn 28 from Röhm & Haas | 0.4 |
| Ceteareth-33 | 2 |
| Sequestrants, stabilizers | qs |
| Phosphoric acid | qs pH = 2.2 ± 0.2 |
| Water | qs 100 |

Process for Dyeing Keratin Fibres

A composition (M) for dyeing keratin fibres is prepared in a bowl according to the following steps:

(1) 100 coated solid particles (i.e. 6 g) according to table 4 above, 58 coated solid particles (i.e. 3.48 g) according to table 6 above, 22 coated solid particles (i.e. 1.32 g) according to table 5 above, 21 coated solid particles (i.e. 1.26 g) according to table 7 above, and 14 coated solid particles (i.e. 0.84 g) according to table 8 above, are mixed with 12 g of oxidizing composition according to table 9 above and 36 g of stabilized water adjusted to pH 2.2; and then, after at least 30 seconds (2) the mixture obtained in step (1) is mixed with 24 g of thickening composition according to table 12 above, 28.8 g of alkaline composition 1 according to table 10 above and 19.2 g of alkaline composition 2 according to table 11 above.

A homogeneous aqueous composition (M), in which the coated solid particles are dispersed in the composition, is thus obtained.

Composition (M) obtained is then applied to locks of natural Caucasian hair containing 90% grey hairs (locks of NG hair) in a proportion of 10 g of composition (M) per 1 g of hair. After a leave-in time of 30 minutes at 27° C., the locks are rinsed, washed with a standard shampoo, rinsed again and then dried.

L, a, b Results:

The colorimetric data for each of the locks are then measured in the CIELab system with a Data Color SF600X spectrophotometer (illuminant D65, angle 100 and specular component included). In this L*a*b* system, L* represents the lightness, a* indicates the green/red colour axis and b* indicates the blue/yellow colour axis. The higher the value of L*, the lighter or less intense the colour. Conversely, the lower the value of L*, the darker or more intense the colour. The higher the value of a*, the redder the shade, and the higher the value of b*, the yellower the shade.

The colour build-up on the hair thus corresponds to the variation in colouring between the locks of dyed NG hair and the locks of undyed (i.e. untreated) NG hair and is measured by the ΔE according to the following equation:

$$\Delta E = \sqrt{(L^* - L_0^*)^2 - (a^* - a_0^*)^2 - (b^* - b_0^*)^2}$$

In this equation, L*, a* and b* represent the values measured after dyeing of the NG hair, and $L_0^*$, $a_0^*$ and $b_0^*$ represent the values measured for the untreated NG locks of hair. The higher the ΔE value, the better the build-up of the colouring.

The results are collated in the table below:

TABLE 13

|  | L* | a* | b* | ΔE |
| --- | --- | --- | --- | --- |
| Lock of untreated NG hair | 57.78 | 1.40 | 13.97 | — |
| Lock of treated NG hair | 23.57 | 2.39 | 5.25 | 35.32 |

It is seen from the results of the table that the keratin fibres treated with composition (M) prepared using solid particles according to the invention are dyed intensely and with a good colour build-up.

It was also found that composition (M) is easy to prepare and to spread on the locks of hair, notably without any running.

Physical Characteristics of the Coated Solid Particles

The physical characteristics of the coated solid particles according to Table 8 above were measured.

The height of this coated solid particle was measured at 4.9 mm, using a vernier caliper.

The mass of this coated solid particle was measured at 56.6 mg using a precision balance.

The hardness of this coated solid particle was measured at 3 kPa, using a Pharmatron ST50 machine.

The mean disintegration time in 25 mL of aqueous hydrogen peroxide solution (containing 6% by weight of $H_2O_2$) at 25° C. and at atmospheric pressure of these particles is less than 30 seconds (about 10 seconds), according to the method described previously.

The invention claimed is:

1. A coloring solid particle (1), having a volume of between 25 mm$^3$ and 125 mm$^3$, and comprising:
   a. a core (2) containing one or more dyes chosen from direct dyes and/or oxidation dye precursors; and
   b. an upper coating layer (3) covering said core (2), and containing one or more cellulose ethers.

2. The coloring solid particle according to claim 1, characterized in that the dyes present in the core (2) are chosen from oxidation dye precursors.

3. The coloring solid particle according to claim 1, characterized in that the core (2) contains one or more oxidation bases chosen from para-phenylenediamines, bis(phenyl)alkylenediamines, para-aminophenols ortho-aminophenols and heterocyclic bases, and the corresponding addition salts.

4. The coloring solid particle according to claim 1, characterized in that the core (2) contains one or more oxidation couplers chosen from meta-phenylenediamines, meta-aminophenols, meta-diphenols, naphthalene-based coupling agents, heterocyclic coupling agents, and the corresponding addition salts thereof or the solvates thereof.

5. The coloring solid particle according to claim 1, characterized in that the total content of dye(s) represents from 0.001% to 50% by weight, relative to the total weight of the particle containing same.

6. The coloring solid particle according to claim 1, characterized in that the cellulose ether(s) present in the upper coating layer (3) are chosen from carboxymethylcellulose (CMC), ethylcellulose (EC), hydroxypropylcellulose (HPC), hydroxypropylmethylcellulose (HPMC), methylhydroxyethylcellulose (MHEC), and mixtures thereof.

7. The coloring solid particle according to claim 1, characterized in that the total content of cellulose ether(s) present in the upper coating layer (3) represents from 30% to 99% by weight, relative to the total weight of the upper coating layer (3).

8. The coloring solid particle according to claim 1, characterized in that said core (2) comprises at least one binder chosen from saccharides and derivatives thereof, oligosaccharides and derivatives thereof, polysaccharides and derivatives thereof, polyvinyl alcohol (PVA), and mixtures thereof.

9. The coloring solid particle according to claim 1, characterized in that said core (2) comprises at least one superdisintegrant polymer chosen from crosslinked polymers of vinylpyrrolidone and derivatives thereof, and mixtures thereof.

10. The coloring solid particle according to claim 1, characterized in that said core (2) comprises at least one antioxidant chosen from (a) ascorbic acid, salts thereof and derivatives thereof, (b) salicylic acid, salts thereof and derivatives thereof, and (c) mercaptan and inorganic sulfites and mixtures thereof.

11. The coloring solid particle according to claim 1, characterized in that the upper coating layer (3) comprises one or more pigments.

12. The coloring solid particle according to claim 1, characterized in that it is anhydrous.

13. The coloring solid particle according to claim 1, characterized in that it has a volume of between 30 and 90 mm$^3$.

14. The coloring solid particle according to claim 1, characterized in that it has a hardness of between 2 and 15 kPa.

15. The coloring solid particle according to claim 1, characterized in that the weight ratio of the total mass of said particle (1) to the total mass of the core (2) is between 1.001 and 1.1.

16. A process for preparing an aqueous dye composition M, comprising the mixing of one or more coloring solid particles (1) with at least one aqueous composition A, wherein each coloring solid particle (1) of the one or more coloring solid particles is according to claim 1.

17. The process according to claim 16, characterized in that said aqueous composition(s) A are chosen from an oxidizing aqueous composition A1 comprising one or more chemical oxidizing agents, and/or an alkaline aqueous composition A2 comprising one or more alkaline agents, and/or an aqueous composition A3 comprising one or more thickening polymers.

18. The process according to claim 16, characterized in that one or more coloring solid particles (1) are at least mixed with an oxidizing aqueous composition A1 comprising one or more chemical oxidizing agents, and an aqueous composition A3 comprising at least one anionic associative polymer.

19. A process for dyeing keratin fibres, comprising at least one step of preparing an aqueous dye composition M as defined in claim 16, and then at least one step of applying said aqueous dye composition M to said keratin fibres.

20. The process according to claim 16, comprising the mixing of several different coloring solid particles (1) with at least one aqueous composition A.

21. The process according to claim 16, wherein the dye(s) in the core (2) of said coloring solid particles (1) is(are) different from one coloring solid particle (1) to another.

22. The process according to claim 16, comprising the mixing of the at least one aqueous composition A with:
   a first type coloring solid particle P1 of the one or more coloring solid particles containing only one oxidation dye precursor C1, and a second type coloring solid particle P2 of the one or more coloring solid particles containing only one oxidation dye precursor C2;

wherein the oxidation dye precursor C1 is different from the oxidation dye precursor C2.

* * * * *